(12) United States Patent
Jones

(10) Patent No.: US 12,073,474 B2
(45) Date of Patent: *Aug. 27, 2024

(54) METHOD OF PREDICTING DRILLING AND WELL OPERATION

(71) Applicant: THE HARTFORD STEAM BOILER INSPECTION AND INSURANCE COMPANY, Hartford, CT (US)

(72) Inventor: Richard B. Jones, Georgetown, TX (US)

(73) Assignee: The Hartford Steam Boiler Inspection and Insurance Company, Hartford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 18/075,378

(22) Filed: Dec. 5, 2022

(65) Prior Publication Data

US 2023/0237594 A1 Jul. 27, 2023

Related U.S. Application Data

(63) Continuation of application No. 17/395,260, filed on Aug. 5, 2021, now Pat. No. 11,521,278, which is a
(Continued)

(51) Int. Cl.
*G06Q 50/02* (2024.01)
*E21B 44/00* (2006.01)
(Continued)

(52) U.S. Cl.
CPC ............ *G06Q 50/02* (2013.01); *E21B 47/08* (2013.01); *G06Q 10/06311* (2013.01);
(Continued)

(58) Field of Classification Search
CPC .. G06Q 50/02; G06Q 10/06311; E21B 47/26; E21B 44/00; E21B 47/08
(Continued)

(56) References Cited

U.S. PATENT DOCUMENTS 8,838,426 B2 * 9/2014 Aldred ................. E21B 7/04
703/10
10,861,110 B2 * 12/2020 Chen ..................... G06Q 10/103
(Continued)

OTHER PUBLICATIONS

Maidla et al. ("Rigorous Drilling-Nonproductive-Time Determination and Eliminating Invisible Lost Time", SPE, 2011, pp. 83-84) (Year: 2011).*
(Continued)

*Primary Examiner* — Iftekhar A Khan
(74) *Attorney, Agent, or Firm* — Greenberg Traurig, LLP

(57) ABSTRACT

A method, apparatus and system is provided for assessing risk for well completion, comprising: obtaining, using an input interface, a Below Rotary Table hours and a plurality of well-field parameters for one or more planned runs, determining, using at least one processor, one or more non-productive time values that correspond to the one or more planned runs based upon the well-field parameters, developing, using at least one processor, a non-productive time distribution and a Below Rotary Table distribution via one or more Monte Carlo trials; and outputting, using a graphic display, a risk transfer model results based on a total BRT hours from the Below Rotary Table and the non-productive time distribution produced from the one or more Monte Carlo trials.

20 Claims, 10 Drawing Sheets

Related U.S. Application Data continuation of application No. 15/062,164, filed on Mar. 6, 2016, now abandoned.

(60) Provisional application No. 62/129,615, filed on Mar. 6, 2015.

(51) Int. Cl.
  *E21B 47/08* (2012.01)
  *E21B 47/26* (2012.01)
  *G06Q 10/0631* (2023.01)
  *G06Q 10/0635* (2023.01)
  *G16C 10/00* (2019.01)

(52) U.S. Cl.
  CPC .......... *G06Q 10/0635* (2013.01); *E21B 44/00* (2013.01); *E21B 47/26* (2020.05); *E21B 2200/20* (2020.05); *E21B 2200/22* (2020.05); *G16C 10/00* (2019.02)

(58) Field of Classification Search
  USPC .......................................................... 703/10
  See application file for complete search history.

(56) References Cited

U.S. PATENT DOCUMENTS

| | | | | |
|---|---|---|---|---|
| 11,391,143 B2* | 7/2022 | Johnston | .................... | E21B 7/04 |
| 2005/0209836 A1* | 9/2005 | Klumpen | ......... | G05B 19/41885 |
| | | | | 703/10 |
| 2005/0209866 A1* | 9/2005 | Veeningen | ............. | G06Q 40/03 |
| | | | | 705/4 |
| 2005/0209912 A1* | 9/2005 | Veeningen | ............. | G06Q 10/10 |
| | | | | 705/7.12 |
| 2005/0228905 A1* | 10/2005 | Veeningen | ............. | G06Q 40/08 |
| | | | | 710/1 |
| 2007/0199721 A1* | 8/2007 | Givens | .................. | G06Q 10/06 |
| | | | | 166/382 |
| 2009/0024429 A1* | 1/2009 | Jones | ................. | G06Q 30/0203 |
| | | | | 705/7.38 |
| 2009/0095469 A1* | 4/2009 | Dozier | .................... | E21B 41/00 |
| | | | | 166/250.01 |
| 2011/0161133 A1* | 6/2011 | Staveley | ................. | E21B 47/00 |
| | | | | 705/7.11 |
| 2011/0203845 A1* | 8/2011 | Jamison | .................. | E21B 44/02 |
| | | | | 702/9 |
| 2011/0225111 A1* | 9/2011 | Ringer | ..................... | G06N 7/01 |
| | | | | 706/14 |
| 2012/0150570 A1* | 6/2012 | Samad-Khan | ......... | G06Q 40/06 |
| | | | | 705/4 |
| 2013/0025939 A1* | 1/2013 | Heliot | .................... | G06Q 50/02 |
| | | | | 175/45 |
| 2015/0081221 A1* | 3/2015 | Mancini | ................ | E21B 49/003 |
| | | | | 702/9 |
| 2015/0112949 A1* | 4/2015 | Marland | ............... | G06F 16/244 |
| | | | | 707/688 |
| 2015/0134390 A1* | 5/2015 | Hildebrand | ...... | G06Q 10/06312 |
| | | | | 705/7.15 |
| 2015/0278407 A1* | 10/2015 | Vennelakanti | .......... | E21B 43/00 |
| | | | | 703/7 |
| 2015/0292323 A1* | 10/2015 | Shahri | ................... | E21B 49/003 |
| | | | | 702/9 |
| 2015/0356450 A1* | 12/2015 | Dursun | .................. | E21B 41/00 |
| | | | | 706/12 |
| 2015/0371344 A1* | 12/2015 | Khare | .................... | E21B 3/022 |
| | | | | 705/342 |
| 2016/0092482 A1* | 3/2016 | Haq | ....................... | G06Q 10/06 |
| | | | | 707/754 |
| 2016/0253607 A1* | 9/2016 | Xu | ......................... | G06Q 10/06 |
| | | | | 705/7.28 |
| 2016/0260036 A1* | 9/2016 | Jones | ............... | G06Q 10/06311 |
| 2017/0051582 A1* | 2/2017 | Pabon | ................... | E21B 43/305 |
| 2018/0047116 A1* | 2/2018 | Jones | .................... | G06Q 50/02 |
| 2018/0238127 A1* | 8/2018 | Berry | ..................... | E21B 19/24 |
| 2018/0328112 A1* | 11/2018 | Berry | ..................... | E21B 19/20 |
| 2019/0203588 A1* | 7/2019 | Popp | ...................... | E21B 44/00 |
| 2020/0210954 A1* | 7/2020 | Loi | ......................... | G06Q 30/04 |
| 2020/0277848 A1* | 9/2020 | Johnston | ................ | E21B 44/00 |
| 2021/0372262 A1* | 12/2021 | Machocki | ............... | E21B 43/30 |

OTHER PUBLICATIONS

York et al. ("Eliminating Non-Productive Time Associated With Drilling Trouble Zones", Offshore Technology Conference, 2009, pp. 1-18) (Year: 2009).*

* cited by examiner

| Non-USA Risk Model | | | Risk Modifiers | | Deduct ible | Insured Floor | # of Iterations |
|---|---|---|---|---|---|---|---|
| Total BRT Hours | 1,511 | | On/Off Shore | Time Trend | 0 | 0 | 10,000 |
| % Slack | 10% | | 1.24 | 1 | Time $0 | Financial $0 | |

United Kingdom BRT Risk Analysis by Planned Run: Off Shore

| | Planned Run Parameters | | | | Bottom Hole Assembly Configuration | | | | | | Planned Run Descriptions and Dynamic Variables | | | | | | Limit=120 |
|---|---|---|---|---|---|---|---|---|---|---|---|---|---|---|---|---|---|
| Run # | BRT Hrs | Hole Size Cat. (1-4) | Total Depth Cat. (1-4) | Drilled Length Cat. (1-4) | Dog Leg Cat. (1-4) | Prod. 1 | Prod. 2 | Prod. 3 | Prod. 4 | Prod. 5 | Prod. 6 | Hole Size Interval | Total Depth Interval | Drilled Length Interval | Dog Leg Label | Run Hourly Rate | NPT Freq. | NPT Severity | NPT Risk (hr) | NPT Risk ($) |
| 1 | 10 | 4 | 1 | 1 | 4 | Motor Probe | | | | | | >12.25 | <1000 | <1000 | Long | $1 | 0 | 1.84 | 0.00 | $0 |
| 2 | 53 | 4 | 1 | 1 | 4 | AutoTrak | CoPilot | | | | | >12.25 | <1000 | <1000 | Long | $1 | 0 | 1.84 | 0.00 | $0 |
| 3 | 26 | 4 | 2 | 1 | 4 | AutoTrak | CoPilot | | | | | >12.25 | 1000-5000 | <1000 | Long | $1 | 0 | 1.66 | 0.00 | $0 |
| 4 | 39 | 3 | 2 | 1 | 4 | AutoTrak | CoPilot | | | | | >8.5<=12.25 | 1000-5000 | <1000 | Long | $1 | 0 | 6.28 | 0.00 | $0 |
| 5 | 93 | 3 | 2 | 1 | 4 | AutoTrak | LithoTrak | CoPilot | | | | >8.5<=12.25 | 1000-5000 | <1000 | Long | $1 | 0 | 6.28 | 0.00 | $0 |
| 6 | 10 | 4 | 1 | 1 | 4 | Motor Probe | | | | | | >12.25 | <1000 | <1000 | Long | $1 | 0 | 1.84 | 0.00 | $0 |
| 7 | 48 | 4 | 1 | 1 | 4 | AutoTrak | CoPilot | | | | | >12.25 | <1000 | <1000 | Long | $1 | 0 | 1.84 | 0.00 | $0 |
| 8 | 121 | 4 | 2 | 2 | 4 | AutoTrak | CoPilot | | | | | >12.25 | 1000-5000 | 1000-5000 | Long | $1 | 0 | 8.53 | 0.00 | $0 |
| 9 | 84 | 3 | 2 | 2 | 4 | AutoTrak | CoPilot | | | | | >8.5<=12.25 | 1000-5000 | 1000-5000 | Long | $1 | 0 | 5.85 | 0.00 | $0 |
| 10 | 169 | 3 | 2 | 2 | 4 | AutoTrak | LithoTrak | CoPilot | | | | >8.5<=12.25 | 1000-5000 | 1000-5000 | Long | $1 | 0 | 5.85 | 0.00 | $0 |
| 11 | 10 | 4 | 1 | 1 | 4 | Motor Probe | | | | | | >12.25 | <1000 | <1000 | Long | $1 | 0 | 1.84 | 0.00 | $0 |
| 12 | 45 | 4 | 1 | 1 | 4 | AutoTrak | CoPilot | | | | | >12.25 | <1000 | <1000 | Long | $1 | 0 | 1.84 | 0.00 | $0 |
| 13 | 71 | 4 | 2 | 1 | 4 | AutoTrak | CoPilot | | | | | >12.25 | 1000-5000 | <1000 | Long | $1 | 0 | 1.66 | 0.00 | $0 |

FIG. 2

METHOD OF PREDICTING DRILLING AND WELL OPERATION

CROSS-REFERENCE TO RELATED APPLICATIONS

This application claims the benefit, and priority benefit, of U.S. patent application Ser. No. 17/395,260, filed Aug. 5, 2021, titled "METHOD OF PREDICTING DRILLING AND WELL OPERATION," U.S. patent application Ser. No. 15/062,164, filed Mar. 6, 2016, titled "RISK ASSESSMENT FOR DRILLING AND WELL COMPLETION OPERATIONS," and U.S. Provisional Patent Application Ser. No. 62/129,615, filed Mar. 6, 2015, titled "RISK ASSESSMENT FOR DRILLING AND WELL COMPLETION OPERATIONS," the disclosure of each of which is incorporated herein in its entirety.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

The present invention generally relates to determining and predicting risk based on results from failures that originate from an operator's product and service delivery using a risk transfer model (RTM). Specifically, but not by way of limitation, embodiments of the present invention include quantitatively assessing risk and reliability for drilling and well completion based upon a variety of parameters, such as non-productive time (NPT).

BACKGROUND OF THE INVENTION

In the oil and gas industry, drilling and completing hydrocarbon wells involve a complex process of drilling and other operations. When completing a hydrocarbon well, drilling operators typically run a variety of downhole monitoring equipment within the wellbore to improve well completion effectiveness and profitably. Often times when completing wells, drilling operators are bound to strict timelines and may gauge their performance using variety of performance metrics. In many instances, to remain profitable, the drilling operators may need to exceed the performance metrics and/or complete the wells before the designed timeline. For instance, drilling operators may be evaluated on the performance metric nonproductive time or NPT. In certain instances, if the total NPT time for completing a well exceeds a specified threshold, the drilling operator may be required to pay a penalty equivalent to the damages caused by the excessive NPT. Alternatively, for the same well completion job, the drilling operator may receive bonus compensation if the total NPT time falls under the specified threshold. As such, numerous innovations and improvements are needed to accurately gauge NPT and/or other performance parameters and assess well completion risk.

BRIEF SUMMARY

The following presents a simplified summary of the disclosed subject matter in order to provide a basic understanding of some aspects of the subject matter disclosed herein. This summary is not an exhaustive overview of the technology disclosed herein. It is not intended to identify key or critical elements of the invention or to delineate the scope of the invention. Its sole purpose is to present some concepts in a simplified form as a prelude to the more detailed description that is discussed later.

In one embodiment, a method for assessing risk for well completion, comprising: obtaining, using an input interface, a Below Rotary Table hours and a plurality of well-field parameters for one or more planned runs, determining, using at least one processor, one or more non-productive time values that correspond to the one or more planned runs based upon the well-field parameters, developing, using at least one processor, a non-productive time distribution and a Below Rotary Table distribution via one or more Monte Carlo trials; and outputting, using a graphic display, a risk transfer model results based on a total BRT hours from the Below Rotary Table and the non-productive time distribution produced from the one or more Monte Carlo trials.

In another embodiment, an apparatus for estimating actual downtime from drilling operations using a risk transfer model, comprising: a non-transitory memory, a processor coupled to the non-transitory memory, wherein the processor obtains computer executable instructions stored on a non-transitory memory that when executed by the processor causes the apparatus to perform the following: receive a plurality of field parameters that correspond to a plurality of planned runs via an input interface; determine a non-productive time risk for each of the planned runs based on the field parameters; generate a total non-productive time risk using one or more Monte Carlo trials; and output the total non-productive time risk via a user interface, wherein the number of Monte Carol trials is received via the input interface.

In another embodiment, a system comprising: an input interface, an user interface, a processor coupled the input interface and the user interface, wherein the processor receives computer executable instructions stored on a memory that when executed by the processor causes the following: receive a plurality of field parameters that correspond to a plurality of planned runs via an input interface, determine a non-productive time risk for each of the planned runs based on the field parameters, generate a total non-productive time risk using one or more Monte Carlo trials, and output the total non-productive time risk via a user interface, wherein the number of Monte Carol trials is received via the input interface.

BRIEF DESCRIPTION OF THE DRAWING

For a more complete understanding of this disclosure, reference is now made to the following brief description, taken in connection with the accompanying drawings and detailed description, wherein like reference numerals represent like parts.

FIG. 2 illustrates an embodiment of the displayed RTM on the RTM processing system;

Figure 1:
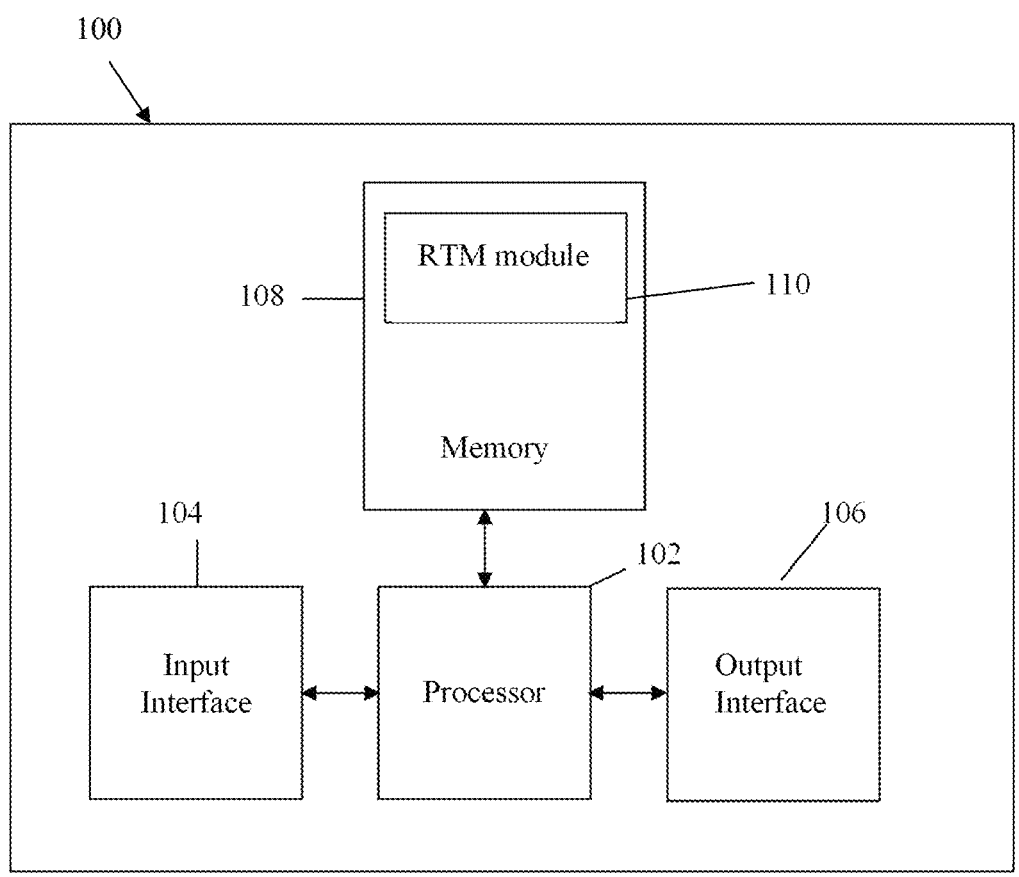
FIG. 1 is a schematic diagram of an embodiment of a RTM processing system.

While certain embodiments will be described in connection with the preferred illustrative embodiments shown herein, it will be understood that it is not intended to limit the invention to those embodiments. On the contrary, it is intended to cover all alternatives, modifications, and equivalents, as may be included within the spirit and scope of the invention as defined by claims to be filed in a subsequent non-provisional patent application. In the drawing figures, which are not to scale, the same reference numerals are used throughout the description and in the drawing figures for components and elements having the same structure, and primed reference numerals are used for components and elements having a similar function and construction to those components and elements having the same unprimed reference numerals.

DETAILED DESCRIPTION

It should be understood that, although an illustrative implementation of one or more embodiments are provided below, the various specific embodiments may be implemented using any number of techniques known by persons of ordinary skill in the art. The disclosure should in no way be limited to the illustrative embodiments, drawings, and/or techniques illustrated below, including the exemplary designs and implementations illustrated and described herein. Furthermore, the disclosure may be modified within the scope of the appended claims along with their full scope of equivalents.

Disclosed herein are various example embodiments that produces and implements a quantitative RTM that accounts for a variety of well-field characteristics that include, but are not limited to drilling time, location, downhole tools used, distance drilled, and well conditions. The RTM may standardize key performance indicators that may be used to differentiate drilling operators' products and services in the marketplace. The RTM may comprise a NPT parameter that indicates well failures from the product or service delivery of the drilling operator(s). Other well failures, such as failure operating outside specification, non-product or service delivery not impacted by the drilling operator(s), product relevant notification and in-house product functional failure may be omitted in assessing a drilling operator(s) NPT performance.

In one embodiment, the RTM may be used to set and price insurance structures and coverage limitations. For example, the RTM may provide a more competitive edge in drilling operation tenders, promote continuous performance improvement in drilling operations, and generate operational key performance indicators that can be financially interpreted and measured by oil field personnel.

FIG. 1 is a schematic diagram of an embodiment of a RTM processing system 100 that may correspond to or may be part of a computer and/or any other computing device, such as a workstation, server, mainframe, super computer, and/or database. The RTM processing system 100 includes a processor 102, which may be also be referenced as a central processor unit (CPU). The processor 102 may communicate (e.g., via a system bus) and/or provide instructions to other components within the RTM processing system 100, such as the input interface 104, output interface 106, and/or memory 108. In one embodiment, the processor 102 may include one or more multi-core processors and/or memory (e.g., cache memory) that function as buffers and/or storage for data. In other words, processor 102 may be part of one or more other processing components, such as application specific integrated circuits (ASICs), field-programmable gate arrays (FPGAs), and/or digital signal processors (DSPs). Although FIG. 1 illustrates that processor 102 may be a single processor, processor 102 is not so limited and instead may represent a plurality of processors. The processor 102 may be configured to implement any of the methods described herein.

FIG. 1 illustrates that the processor 102 may be operatively coupled to one or more input interfaces 104 configured to obtain drilling data for one or more wells sites and one or more output interfaces 106 configured to output and/or display the simulated RTM results, inputted drilling data, and/or other field drilling information. The input interface 104 may be configured to obtain the drilling data via electrical, optical, and/or wireless connections using one or more communication protocols. In one embodiment, the input interface 104 may be a network interface that comprises a plurality of ports configured to receive and/or transmit data via a network. In particular, the network may transmit the drilling data via wired links, wireless link, and/or logical links. Other examples of the input interface 104 may include keyboards, mice, universal serial bus (USB) interfaces, CD-ROMs, DVD-ROMs and/or onscreen input devices (e.g., onscreen keyboard). The output interface 206 may include, but is not limited to a graphic display (e.g., monitors and display screens), a user interface, and/or an interface used to connect to a printing device configured to produce hard-copies of the generated results.

In addition, FIG. 1 also illustrates that memory 108 may be operatively coupled to processor 102. Memory 108 may be a non-transitory medium configured to store various types of data. For example, memory 108 may include one or more memory devices that comprise secondary storage, read-only memory (ROM), and/or random-access memory (RAM). The secondary storage is typically comprised of one or more disk drives, optical drives, solid-state drives (SSDs), and/or tape drives and is used for non-volatile storage of data. In certain instances, the secondary storage may be used to store overflow data if the allocated RAM is not large enough to hold all working data. The secondary storage may also be used to store programs that are loaded into the RAM when such programs are selected for execution. The ROM is used to store instructions and perhaps data that are read during program execution. The ROM is a non-volatile memory device that typically has a small memory capacity relative to the larger memory capacity of the secondary storage. The RAM is used to store volatile data and perhaps to store instructions.

As shown in FIG. 1, the memory 108 may be used to house the instructions for carrying out various embodiments described herein. In an embodiment, the memory 108 may comprise a RTM module 110 that may be accessed and implemented by processor 102. Alternatively, RTM module 110 may be stored and accessed within memory embedded in processor 202 (e.g., cache memory). Specifically, the RTM module 110 may receive a variety of inputted information relating to field parameters for one or more wells and quantify risks associated with future well completions. The RTM analysis may involve transforming acquired raw drilling data into a new data base where the actual run data is summed to produce a new data set where each record is a planned run.

In assessing and quantifying risks, the unit of exposure of risk for well construction may be identified as a "planned run." The term "planned run" is defined throughout this disclosure as how drilling operator(s) plan to drill a well. A "planned run" may constitute a specific hole size, drilled length, dog leg (for directional drilling), and bottom hole assembly. For example, a drilling operation for completing a well may on average have about 5 planned runs because of the different hole or piping sizes. An actual run corresponds to number of instances the drilling operators has to actually insert and remove a tool string when drilling a well. Typically, a drilling operation may average more than 20 actual runs for jobs estimated with about 5 planned run. In practice more actual runs are compiled than the "planned run" because of equipment failures and various other situations that may require the drilling operator to stop drilling and pull the tool string out of the wellbore.

Non-productive time extends a drilling period but does not include or determine all of the actual drilling time. Well planners may utilize previous field drilling experience and simulations to estimate how long each planned run will take in real hours assuming the drilling period has about zero NPT. The estimated time for a planned run is referenced throughout this disclosure as Below Rotary Table (BRT) hours. In other words, BRT hours is an estimate of how long a drilling operator may take to finish drilling that includes not just pure drilling time, but also tripping and logging time. NPT extends the drilling period by adding the NPT risk distribution to the computed BRT hours to determine the total time for drilling, which includes the time for tool failures. BRT hours may be the RTM's model output variable even though the RTM analysis is based on NPT. Uncertainty in BRT determination are addressed by the RTM analysis and will be discussed later in the disclosure. Non-productive time for product or service delivery with influenced (PSDI) may be used as one of the main risk variables in well drilling operations.

The BRT distribution may be important regarding tenders from customers of drilling operators. The tenders may be based on the time to drill a specific number of wells and not by individual run parameters. In one embodiment, the BRT distribution may be the dominant (and most complex) part of the time to well completion equation. In other embodiments, other elements of a well can be analyzed and considered using the RTM, such as completion (packer and liner setting) and artificial lift (pumping).

In one embodiment, the RTM may comprises four field-based actuarial variables: hole size (inches), drilling depth (feet (ft.)), drilled length (ft.), and maximum dog leg. Hole size may be a direct measurement based on contract specifications and/or the implementation plan regarding the size of the hole to be drilled for a well. Drilling depth may be computed as the current maximum depth of a well, the drilled distance may correspond to the drilled length, and dog leg, which may be expressed in degrees/100 ft., may reference the maximum direction change for the planned run. The field-based actuarial variables may be chosen due to their physical nature that makes them relatively easy to measure and also as variables that may be shown to influence NPT risk. Each variable may be categorized in a manner that reflects both the engineering exposure and the availability of data to suitably represent the risk characteristics. For example, Table 1 illustrates an example embodiment of category definitions that may be used in the RTM analysis:

TABLE 1

| Hole Size Cat | Hole Size Range | Depth Category | Depth Category Range | Drilled Length Category | Drilled Length Category Range | Dog Leg Category | Category Label | Degrees/100 ft |
|---|---|---|---|---|---|---|---|---|
| 1 | <=6.25 | 1 | <1,000 | 1 | <1,000 | 1 | Short | >70, <=180 |
| 2 | >6.25<=8.5 | 2 | 1,000-5,000 | 2 | 1,000-5,000 | 2 | Inter | >40, <=70 |
| 3 | >8.5<=12.25 | 3 | 5,000-10,000 | 3 | 5,000-10,000 | 3 | Med | >6, <=40 |
| 4 | >12.25 | 4 | 10,000+ | 4 | 10,000+ | 4 | Long | <=6 |

Other variables may be added or the category criteria may be modified depending on the field characteristics of the well site. The variables and category criteria included in the RTM may be used to generate NPT event frequency, severity, and risk with suitable data populations in order to provide the required statistical significances.

The RTM's basic drilling information may be computed by "planned run." In one embodiment, a user or analyst may enter raw drilling data for the planned BRT hours, the hole size, maximum depth, drilled length, dog leg category, and the bottom hole assembly configuration for each planned run. In another embodiment, the raw drilling data may be imported and/or downloaded from one or more pre-existing data files. The data entered and/or obtained could be for a single well with multiple planned runs or runs planned to be executed for several wells. For example, a project plan for drilling four off shore wells in the United Kingdom may appear as shown in Table 2.

TABLE 2

| BRT | Hole Size | Max Depth | Drilled Length | Max Dogleg | BHA Products |
|---|---|---|---|---|---|
| 10 | 36 | 100 | 100 | 4 | Prod # 62 Prod # 29 |
| 52.6 | 26 | 707 | 607 | 4 | Prod # 37 Prod # 12 |
| 26.2 | 17.5 | 1010 | 403 | 4 | Prod # 71 Prod # 75 |
| | | | | | Prod # 57 Prod # 60 |
| 68.7 | 12.25 | 1890 | 1487 | 4 | Prod # 47 Prod # 8 |
| | | | | | Prod # 18 Prod # 32 |
| 32.5 | 9.5 | 2790 | 1303 | 4 | Prod # 17 Prod # 76 |
| | | | | | Prod # 10 Prod # 18 |
| 12 | 36 | 100 | 100 | 4 | Prod # 84 Prod # 2 |
| 33 | 26 | 687 | 587 | 4 | Prod # 24 Prod # 79 |
| 124 | 17.5 | 2145 | 1558 | 4 | Prod # 28 Prod # 63 |
| 88 | 12.25 | 3154 | 1596 | 4 | Prod # 64 Prod # 31 |
| 158 | 9.5 | 4789 | 3193 | 4 | Prod # 47 Prod # 17 |
| 8.6 | 36 | 95 | 95 | 4 | Prod # 53 Prod # 75 |
| 44.4 | 26 | 654 | 559 | 4 | Prod # 36 Prod # 43 |
| 71.3 | 17.5 | 1765 | 1206 | 4 | Prod # 80 Prod # 67 |
| 22.3 | 12.25 | 1876 | 670 | 4 | Prod # 89 Prod # 79 |
| 66.5 | 9.5 | 2456 | 1786 | 4 | Prod # 66 Prod # 20 |
| 67.3 | 9.5 | 2678 | 892 | 4 | Prod # 11 Prod # 17 |
| 5.9 | 36 | 90 | 90 | 4 | Prod # 89 Prod # 38 |

TABLE 2-continued

| BRT | Hole Size | Max Depth | Drilled Length | Max Dogleg | BHA Products |
|---|---|---|---|---|---|
| 76 | 26 | 902 | 812 | 4 | Prod # 37 Prod # 53 |
| 144.3 | 17.5 | 2534 | 1722 | 4 | Prod # 34 Prod # 90 |
| 108.4 | 12.25 | 3754 | 2032 | 4 | Prod # 24 Prod # 28 Prod # 71 Prod # 48 |
| 57.9 | 9.5 | 4665 | 2633 | 4 | Prod # 90 Prod # 71 Prod # 86 Prod # 32 Prod # 68 |
| 167.7 | 9.5 | 5432 | 2799 | 4 | Prod # 24 Prod # 22 Prod # 81 Prod # 63 Prod # 85 |

Subsequently, the RTM and/or user may convert the acquired raw drilling data into data used in the RTM data base. FIG. 2 illustrates an example on how the raw data is converted and/or entered into the RTM. As shown in FIG. 2, the RTM or user enters the category numbers and other data only in the gray sections based on the acquired raw drilling data. For the planned run entries, the corresponding labels are automatically completed in the columns with the blue headers to provide a visual check that the correct data is being entered. The other columns are used by the RTM to access the corresponding NPT event frequency and severity distributions for the entered category sequences.

As shown in FIG. 2, the RTM parameters or variables include hole size, depth, drilled length, and bottom hole assembly data supplied for each planned run. The NPT event frequency may be a direct function of the bottom hole assembly configuration. Failure of this assembly may be the originating cause of NPT. For well drilling and construction, the probability of a failure of the bottom hole assembly configuration may drive NPT event frequency. NPT severity may be computed to include modification factors for hole size, depth, drilled length and maximum dog leg. These factors are viewed as environmental factors which influence NPT risk. NPT severity may be a function of the time required to remove a failed bottom hole assembly and re-insert a new one. From the data, four statistically significant distributions may be determined, which will be discussed in more detail below. They are individually assigned to planned run sequence distributions as a function of their hole size, depth, and drilled length categories. The maximum dog leg value may represent a risk modifier as a function of hole size and dog leg parameters.

NPT and BRT distributions may be statistically developed via a Monte Carlo method with the number of trials being supplied by the user as an input parameter. Persons of ordinary skill in the art are aware that a Monte Carlo method typically follows that pattern of determining a domain of possible inputs, generates inputs randomly from a probability distribution over the domain, perform a deterministic computation on the inputs, and aggregate the results. Specifically for NPT and BRT distributions, each planned run is first tested to check for the occurrence of an NPT failure event of the run's bottom hole assembly. In one embodiment, the test outcome may be represented as binary with 0 for no failure and 1 for a failure. The NPT severity distribution for each planed run may then be multiplied by the binary frequency function to compute the planned run NPT risk. The NPT risk value may then be modified by factors to account for the specific hole size, depth, drilled length, and maximum dog leg values. The product may be the risk adjusted NPT risk value for every planned run. After each planned run has been computed, the NPT risk values may be summed over the total set of runs under analysis to compute total NPT risk for one Monte Carlo trial. This method may continue to repeat itself as many times as specified by the user (e.g., user provides information on an input screen) and the statistical analysis of the Monte Carlo process forms the basis of output results. The total BRT hours may be added to the NPT risk distribution to produce output statistics that have direct application to well completion times.

In one embodiment, to translate the determined NPT risk to another quantifiable risk, such as financial risk, a matrix may be defined in the model reference section that introduces the dollar cost (or loss) per hour of NPT as a function of hole size, depth, and drilled length. This information is entered by the user based on the value of the wells being completed. For example, the NPT time and financial risk may be computed for each planned run and aggregated over all planned runs. The aggregate NPT value may then be added to the total BRT hours to produce the total time to well (or wells) completion distribution.

In one embodiment, the produced output statistics from the FTM may not represent or account for specific local operating conditions. To be applicable to insuring minimum levels of performance (API) for a specific contract tender, the RTM may be adjusted to reflect three conditions: (1) The specific country or field; (2) The distribution of well risks that are land & off-shore; (3) and the future.

Figure 3:
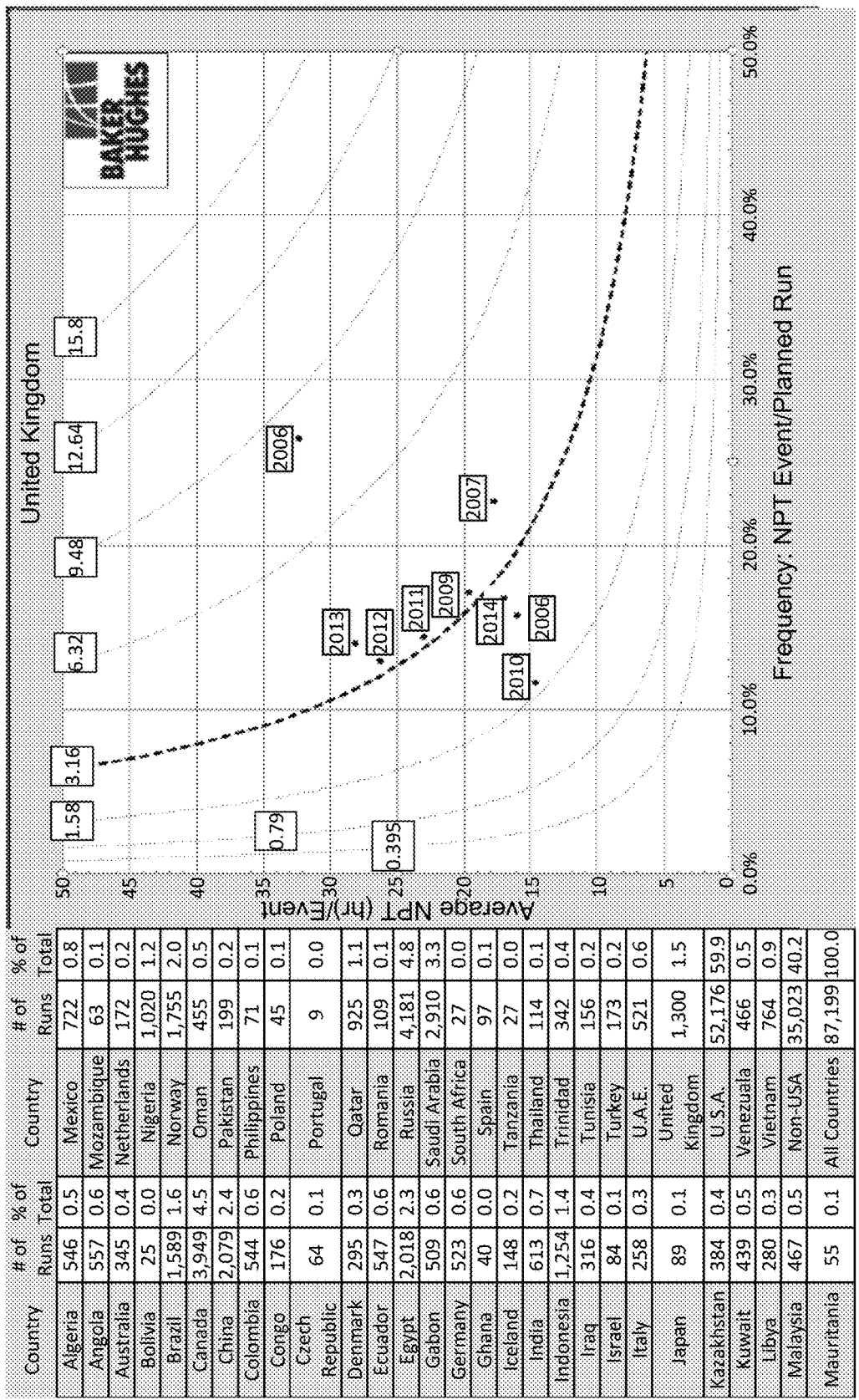
FIG. 3 illustrates a "Country RM" tab used by the RTM.

The RTM, as shown in FIG. 2, allows for about three risk modifiers to customize the results to these conditions. The "Location" modifier may be a factor that is computed based on the analysis of the data shown in the RTM's "Country RM" tab, which is shown in FIG. 3. Referring to FIG. 3, the user may initially select the country of interest and subsequently using an input interface (e.g., click on a run button) to update the plot within the RTM. The numbers next to the country name represent the percentage of total records that are from each country. This information may inform the user about the general amount of data or drilling activity that has been performed in each country which implicitly relates to the statistical reliability of the risk frequency, severity, and risk results.

The graph's horizontal axis represents the NPT event frequency measured in terms of number of NPT events per planned run. The vertical axis is the NPT event severity: average NPT duration per event in hours. The curved lines on the plot are iso-risk contours. Along each line, the product of frequency and severity has the same value. The small boxes illustrate the value of each iso-risk contour. In FIG. 3, the heavy dotted line may represent a Non-USA average (well sites located outside for a drilling operator) over the entire data range for a specified time range corresponding to the acquired raw data (e.g., from 2006 to 2014-Quarter 3). The points show the NPT frequency, severity, and risk for each year for the selected country (e.g., United Kingdom in FIG. 3) for a drilling operator.

In FIG. 3, each point represents the annual average NPT performance for the selected country. The general computational results can be customized to a specific country by taking the ratio of a particular year's risk value to the overall average: 3.16. For example, consider the country risk modification factor to replicate the 2006 results for the United Kingdom. The iso-risk contour for the 2006 point can be computed by multiplying the 2006 coordinates together or via approximately by visually interpolating between the displayed iso-risk contours. In one embodiment, the RTM may display the precise coordinates by having the user placing the cursor over the interested point. In FIG. 3, the coordinates are 26.6% and 32.29 which produce the iso-risk contour of 8.56. The 2006 United Kingdom country risk modifier may be computed as 8.56/3.16=2.7. The computed risk modifier may be the value entered on the RTM model input screen as the Country Risk Modifier shown in FIG. 2. For 2010 the risk modifier may be about 1.56/3.16 or about 0.5, and for 2014, the Country Risk Multiplier may be approximately 1.0.

Trending the information output by the RTM into the future may include data generated beyond the arithmetic operations previously discussed above. The plot can provide information on historical trends in frequency, points consistently moving left or right, severity—points moving consistently up or down, and risk points consistently moving diagonally. To generate a future risk score, the trend (or pattern) of the frequency, severity, and risk data is extrapolated and applying factors associated with operational data and having a performance improvement plan in place. For example, if there are robust training programs in place or comprehensive root cause activities, then the user can apply this knowledge to input, for example, that the future NPT will be 25% less than the current year's results. The use of operational data along with the risk-based time performance results presented in the specialized graphic format provides a "real time" data-driven approach to estimate future NPT performance.

Field specific information inside a country may be extracted and formatted from one or more database and local operation reports so that it can be presented in the frequency-severity format used for the country risk multiplier in the RTM. A process similar to the country risk multiplier development can be applied to compute a field risk modifier. The field risk modifier factor may then be multiplied by the country risk multiplier to adjust the generalized model results to a specific country and field. In one embodiment, the general model results may combine land and offshore NPT performance risk. In some instances the acquired drilling data may not specify operational type, and thus, may not separate land and off-shore operations from the location or country in the dataset. The acquired drilling data may indicate that the majority of countries are dominated by one type of drilling so in most cases, and thus, computing the country (and field) multipliers may be sufficient to adjust the results to actual performance. In another embodiments, the acquire drilling data may specify land and off-shore operations and could be computed and applied similar to the country risk and field risk modifiers as discussed above.

Figure 4:
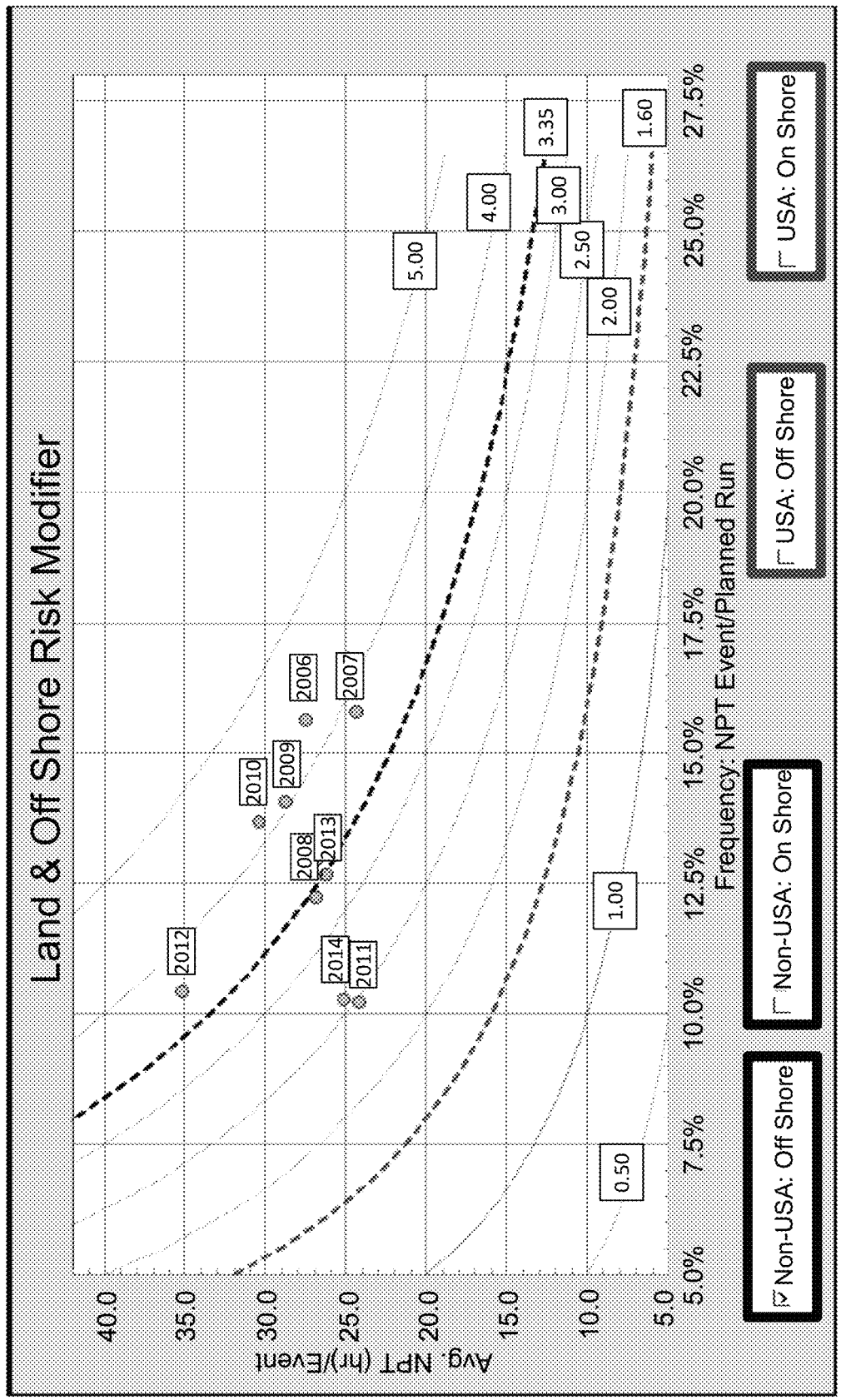
FIG. 4 illustrates an embodiment of the NPT event frequency, severity, and risk, by year, location, land and offshore.

In one embodiment, the NPT event frequency, severity, and risk, by year, location, land and offshore as shown in FIG. 4 may include a trend (or pattern) information to assist the user in forecasting future NPT performance by operational location. The RTM allows for the user to adjust the general results based on insights the users gain by combining the risk-based information with the user's operational knowledge. The multiplier is set to unity by default. The user can change this factor by entering their choice in the land and off-shore cell on the input data screen as shown in FIG. 2.

The Time "Trend" cell as shown in FIG. 2 of the input data screen is a free form element constructed for the user to add another adjustment factor to the generalized results based on future drilling operations data for the planned runs listed in the input data screen. The Time "Trend" cell could also be used for the field multiplier previously discussed. Entering this value here helps document the run values for future reference in order to increase the user's understanding of how to apply the risk model for forecasting future NPT risk results.

The generalized results are computed from the stochastic analysis of each record in the input data screen. The NPT time risk equation for each record 'K' is as shown in equation (1):

$$\text{NPT Time Risk}(h,d,l,t)k = \text{Prob Fail}(BHAk) * \max\{\text{Sev}(h,d,l) * \text{Dogleg}(h,r), \text{Severity Limit}\} * CR * SH * TR \quad (1)$$

where "h" represents hole size category, "l" represents the drilled length category, "d" represents the depth category, "t" represents the maximum dog leg category. Additionally, Prob Fail(BHAk) represents the probability of failure of the BHA for planned run 'k'; Sev(h, d, l) represents the NPT time severity distribution (e.g., one of four) assigned to the hole size, depth, and drilled length categories; and Dogleg(h, r) represents the Dog leg modifier as a function of hole size and turn rate; Severity Limit represents the maximum value allowed for a single NPT event for all planned run severity calculations; CR represents Country risk modifier; SH represents Land/Off-shore risk modifier; and TR represents Trend risk modifier.

The Severity Limit may be entered once at the beginning of an analysis and applies to all subsequent severity calculations. The actual severity distributions may be by construction unbounded on the upper side. Consequently, they can produce NPT downtime values that may be relatively large for the actual situations being modeled as judged by the user. For example, suppose that for a specific planned run, the drilling operator's actual operational data (and therefore distribution fitted to this data) indicates that NPT event times could exceed 30 days. However, based on the logistic data and condition data associated with the specific set of wells under analysis, a user selection can be made to use a maximum value for any single run of 5 days. Setting this upper limit recognizing local logistic and operational environmental data is another way the user can make data input selections to customize the RTM to a specific set of conditions. By setting the Severity Limit to a relatively large number, such as about 9,999, the user can utilize the full variation of NPT values produced by the distributions constructed by the underlying NPT severity data.

In the embodiment, the NPT financial risk may include an additional term, HourRate(h, d, l), to the NPT Time risk that converts NPT time to financial costs as shown in equation 2:

$$\text{NPT Cost Risk}(h,d,l,t)k = \text{Prob Fail}(BHAk) * \max\{\text{Sev}(h,d,l) * \text{Dogleg}(h,r), \text{Severity Limit}\} * CR * SH * TR * \text{HourRate}(h,d,l) \quad (2)$$

In the RTM used for the NPT financial risk analysis, the cost structure is entered for each hole size, depth, and drilled length combination. As such, the RTM captures non-productive time value through drilling characteristics. With additional data, the RTM is capable of providing different valuation approaches for time to well completions. The fundamental stochastic variables of the RTM are the above time and cost equations summed over all planned runs. The total NPT time and cost risk over "N" planned runs for Monte Carlo trial "j" can be expressed as:

$$\text{NPT Time Risk}_j = \sum_{k=1}^{N} \text{NPT Time Risk}(h, d, l, t)_{k,j} \quad (3)$$

$$\text{NPT Cost Risk}_j = \sum_{k=1}^{N} \text{NPT Cost Risk}(h, d, l, t)_{k,j} \quad (4)$$

The statistical results of these two variables constitute the risk management and insurance model variables. Since the data necessary for the financial analysis formulation is incomplete at this time, the RTM's insurance analysis will be described only for the time variable. Since NPT extends the well completion time, we add the total BRT hours as computed in the model's input screen to equation (3) to produce the practical variable of interest: the distribution of time required to complete the wells as described by the planned runs. The BRT slack percentage is a user selected input for the uncertainty in this number. The BRT hours plus the percentage slack amount is plotted on the output risk plots for comparison of the BRT uncertainty with the NPT uncertainty produced from the model calculations.

The BRT uncertainty may not be directly applied to the insurance analysis. Changes in BRT hours are not necessarily under the control of drilling operators since geological, climate, customer requirements, and several other factors can influence this time. However, drilling operators are typically accountable for schedule delays due to the failure of their products and services.

Insurance Analysis

Figure 5:
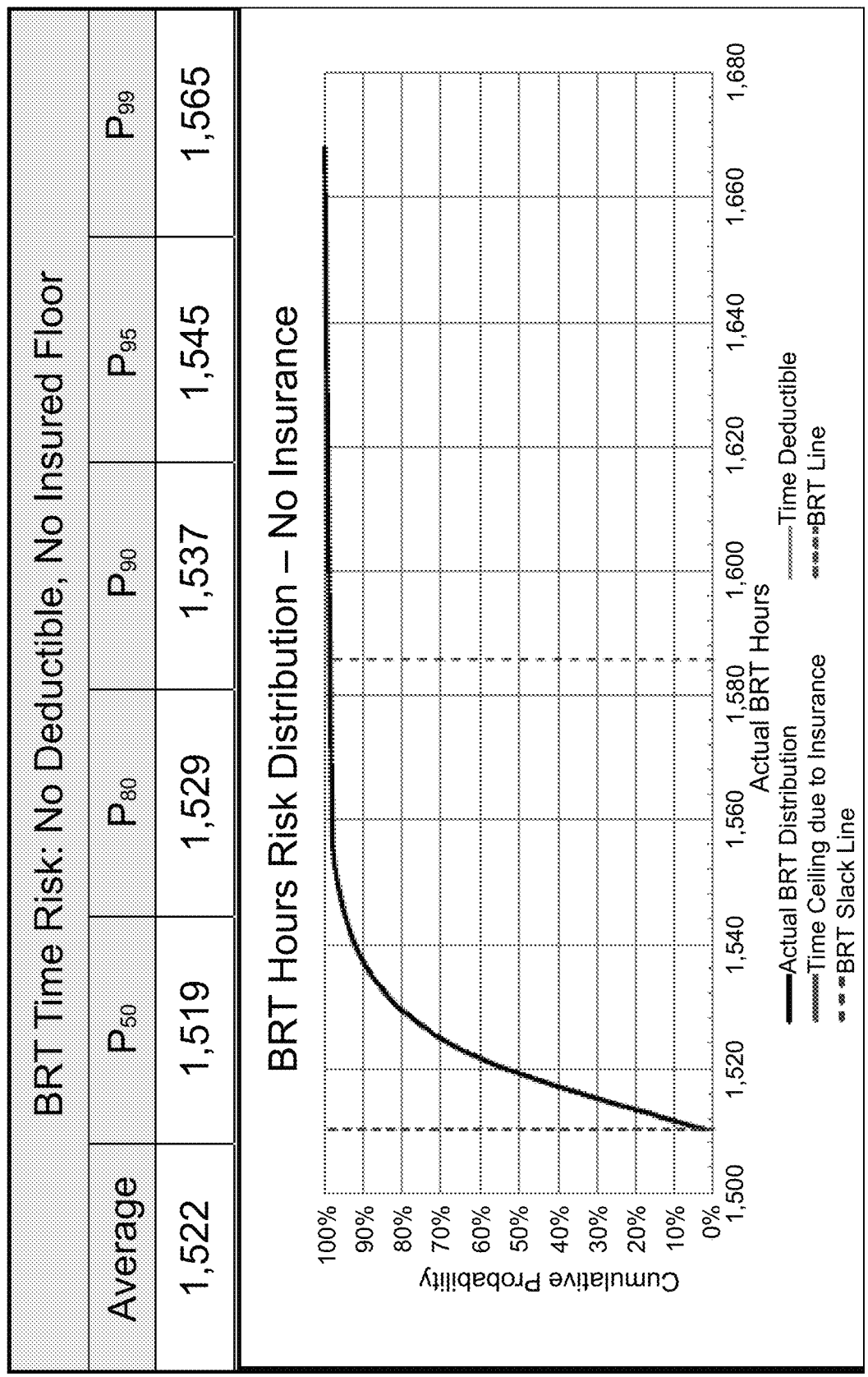
FIG. 5 illustrates an embodiment of running an RTM for 22 planned runs with 10,000 Monte Carlo trials.

In one embodiment, the insurance analysis contains four parts: (1) well completion time risk without insurance parameters; (2) well completion time risk with a prescribed time deductible; (3) well completion time risk with a prescribed time deductible and a time ceiling; and (4) well completion time risk greater than the time ceiling. A common output format may be used for all parts to facilitate a common understanding of the risks associated with each element. The format as shown in FIG. 5 may be modified depending on the insurance environment. The insurance model features as shown in FIG. 5 may be based on the planned runs example depicted in FIG. 2. The set of 22 runs shown in FIG. 2 are for plans to drill about four wells. Actual tender analysis could consider significantly more or less wells and FIG. 2 is used to only to depict the RTM functionality.

For the well completion time risk without insurance parameters section, this section computes the total BRT risk without any constraints imposed on the BRT distribution. These results present the total risk exposure that the planned runs contain. It forms the basis for quantifying the insurance effect of various deductibles and ceilings (insured floors.) The risk variable for this analysis is equation (3). FIG. 5 illustrates running the RTM for the 22 planned runs with 10,000 Monte Carlo trials.

In FIG. 5, the average and presented percentile statistics are common elements of risk management decision-making. The black line in the plot depicts the entire NPT risk distribution as a cumulative distribution function. For example, the probability value associated with a BRT time of 1,540 hours has about a 90% chance that the total BRT hours will be less than or equal to 1,540 hours or a 10% chance BRT will exceed 1,540 hours. The BRT slack is added to show the relative uncertainty upper limit of BRT hours computed to the BRT increase from NPT. The plot may be used to form the basis for developing insurance parameters that produce the desired level of risk retained by a drilling operator and the amount of risk transferred to an insurer. The other legend components will be addressed below.

Figure 6:
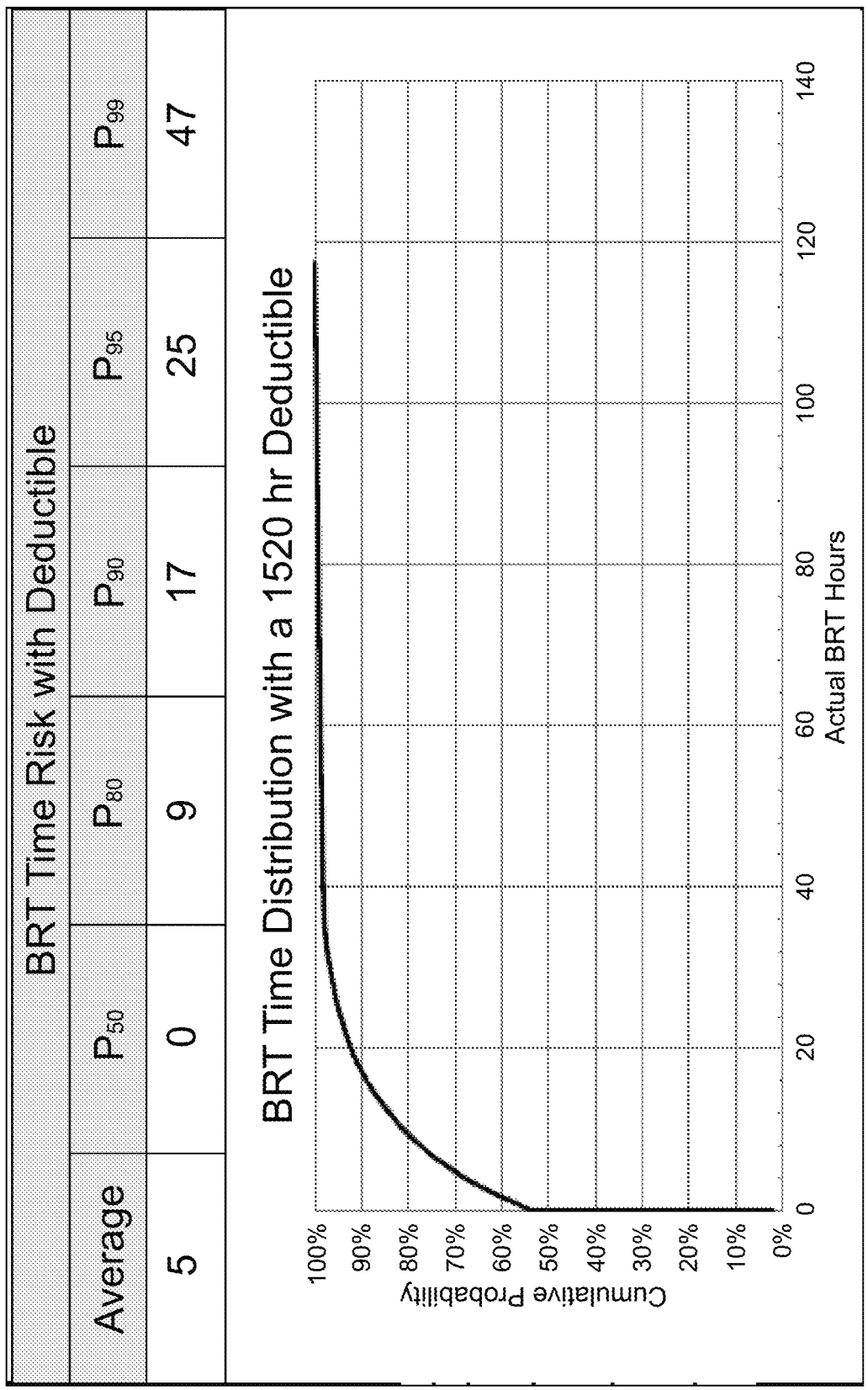
FIG. 6 illustrates an embodiment of the well completion time risk with a prescribed time deductible.
Figure 7:
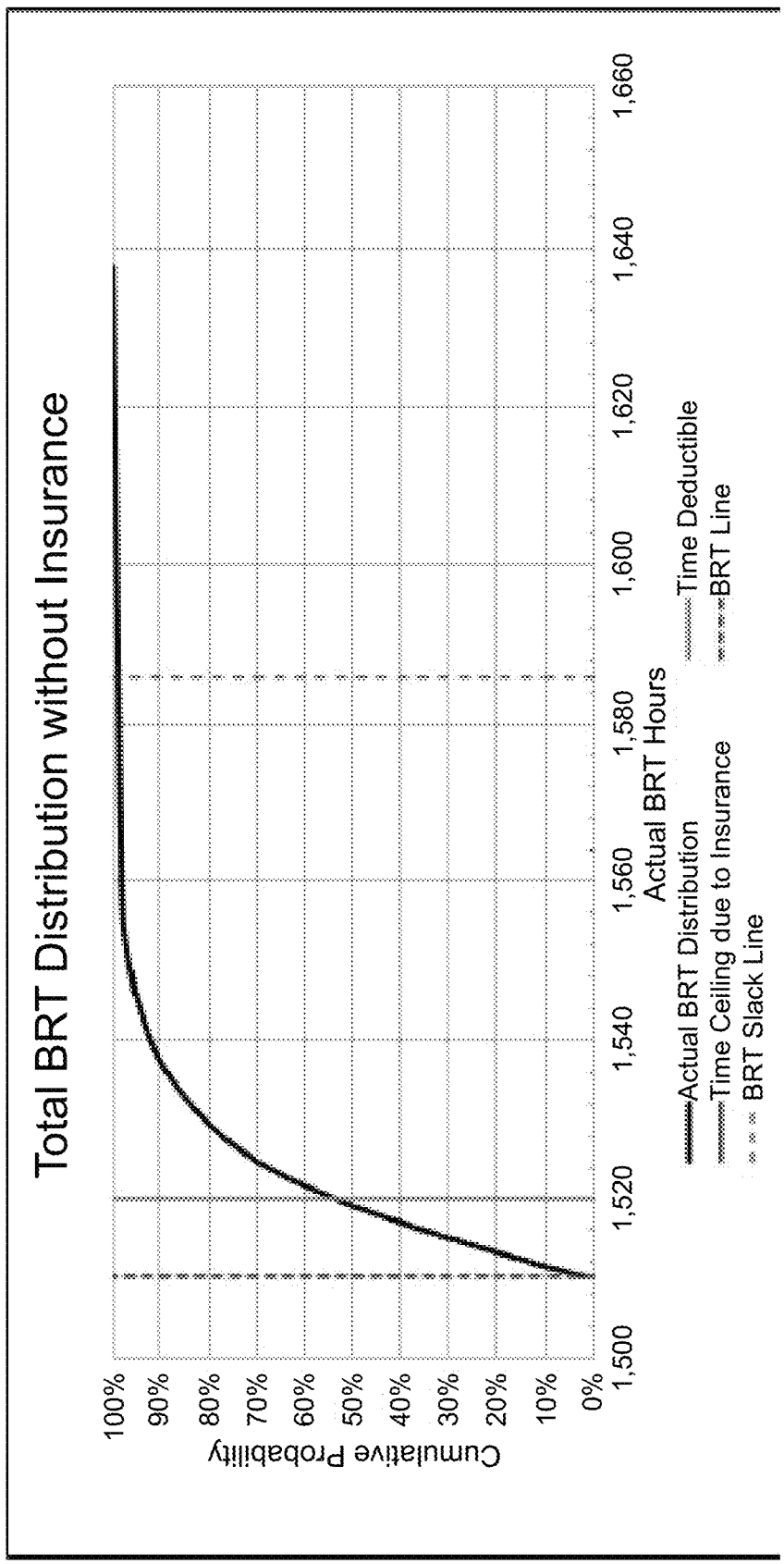
FIG. 7 illustrates an embodiment of an amended distribution based on FIG. 5 that shows the 10 hours NPT deductible from FIG. 6.

FIG. 6 illustrates the well completion time risk with a prescribed time deductible. Using data in FIG. 5 as an example, suppose the customer is willing to accept the risk below the median value of 1,520 hours. There may be no penalty if the BRT is below this threshold. If the BRT exceeds about 1,520 hours, then the service provider may be financially accountable for the time in excess of 1,520 hours. As illustrated in FIG. 6, applying a 1,520 hour deductible produces the results of the risk the service provider is assuming under this scenario. FIG. 6 illustrates the BRT, NPT-based risk distribution that the service provider is assuming by ensuring the total BRT for drilling the 4 wells with the 22 planned runs will be less than or equal to about 1,520 hours. FIG. 7 illustrates an amended distribution based on FIG. 5 that shows the 1,520 hours BRT deductible from FIG. 6.

Figure 8:
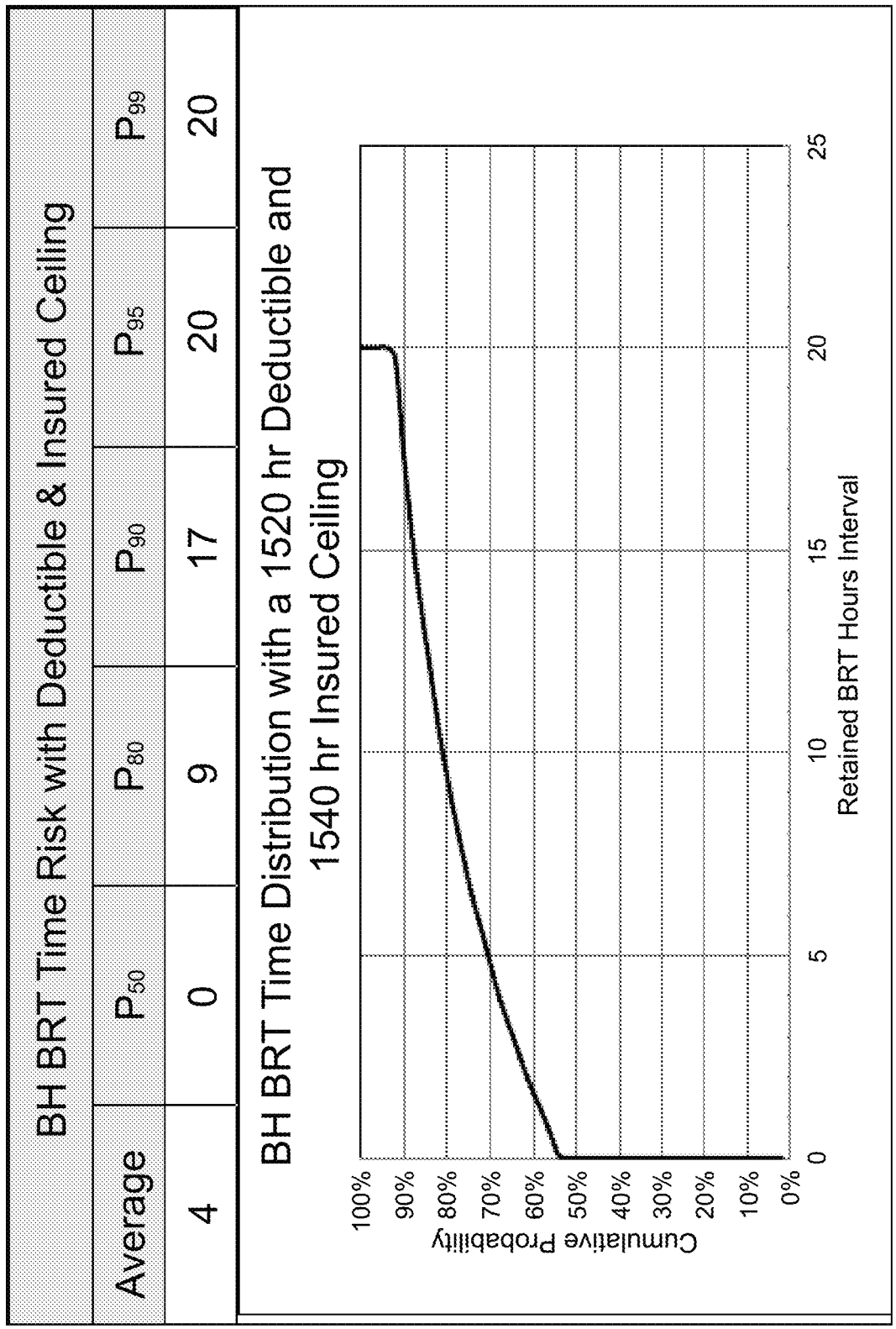
FIG. 8 illustrates an embodiment of the well completion time risk with a prescribed time deductible and a time ceiling.
Figure 9:
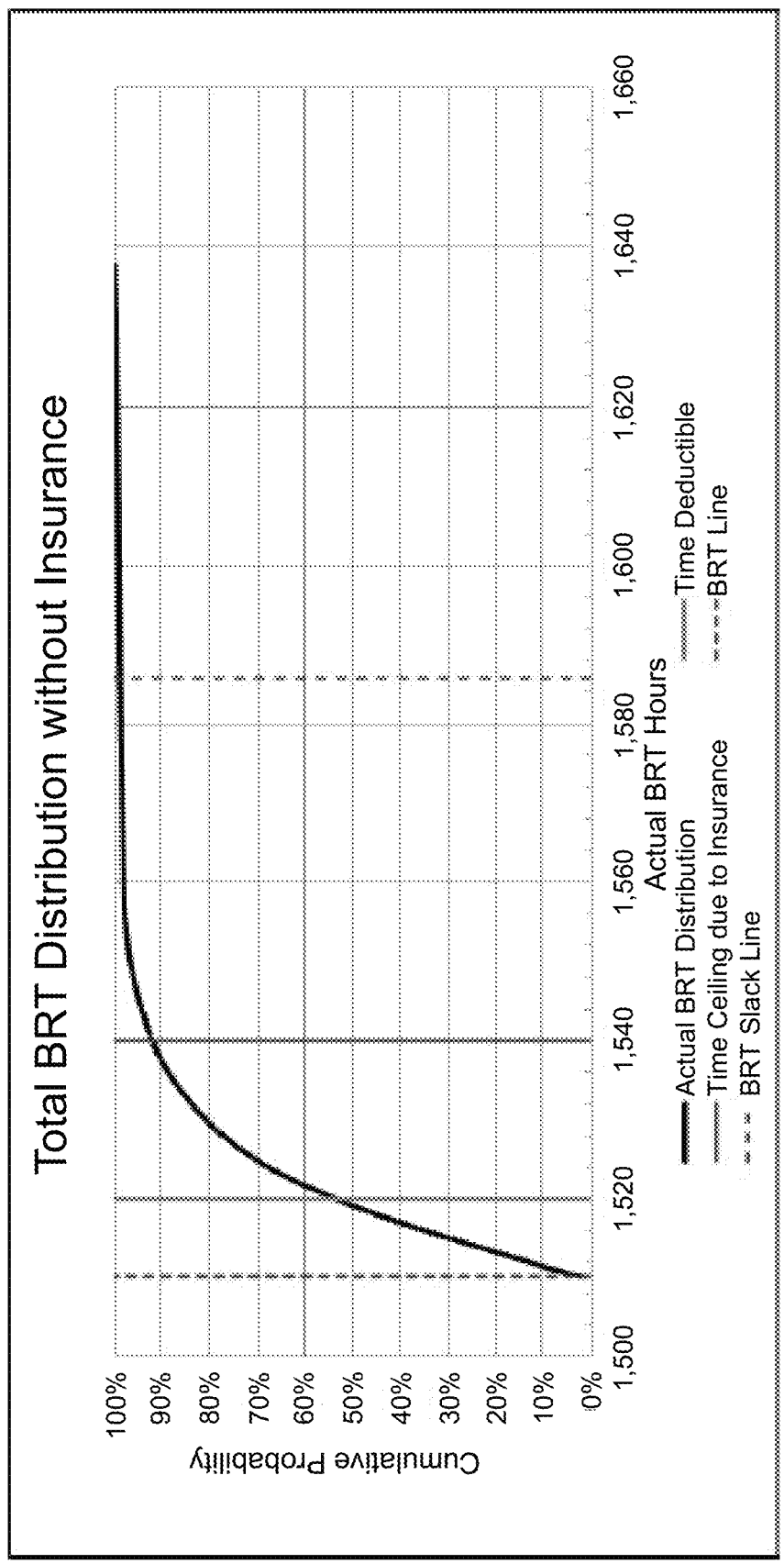
FIG. 9 illustrates an embodiment of an updated distribution based on FIG. 5 that show the risk exposure the drilling operator is retaining.

FIG. 8 illustrates the well completion time risk with a prescribed time deductible and a time ceiling. The plot in FIG. 8 shows that most of the risk is actually for BRT hours greater than 1,520 hours and this where insurance applies. To keep the service provider's risk exposure to a manageable level, an insured floor may be placed at 1,540 hours. From the plot, there may be about a 10% chance that the total non-productive time for drilling the 4 wells would exceed this value. Adding the insured floor or the service provider's risk assumed ceiling produces the plot shown in FIG. 8 and statistical results for the risk exposure they have retained between 1,520 and 1,540 hours. FIG. 9 illustrates an updated distribution based on FIG. 5 that show the risk exposure the drilling operator is retaining. In FIG. 9, this is represented between the blue and red solid vertical lines. The risk exposure is transferred to an insurer, which is to the right of the red vertical line.

Figure 10:
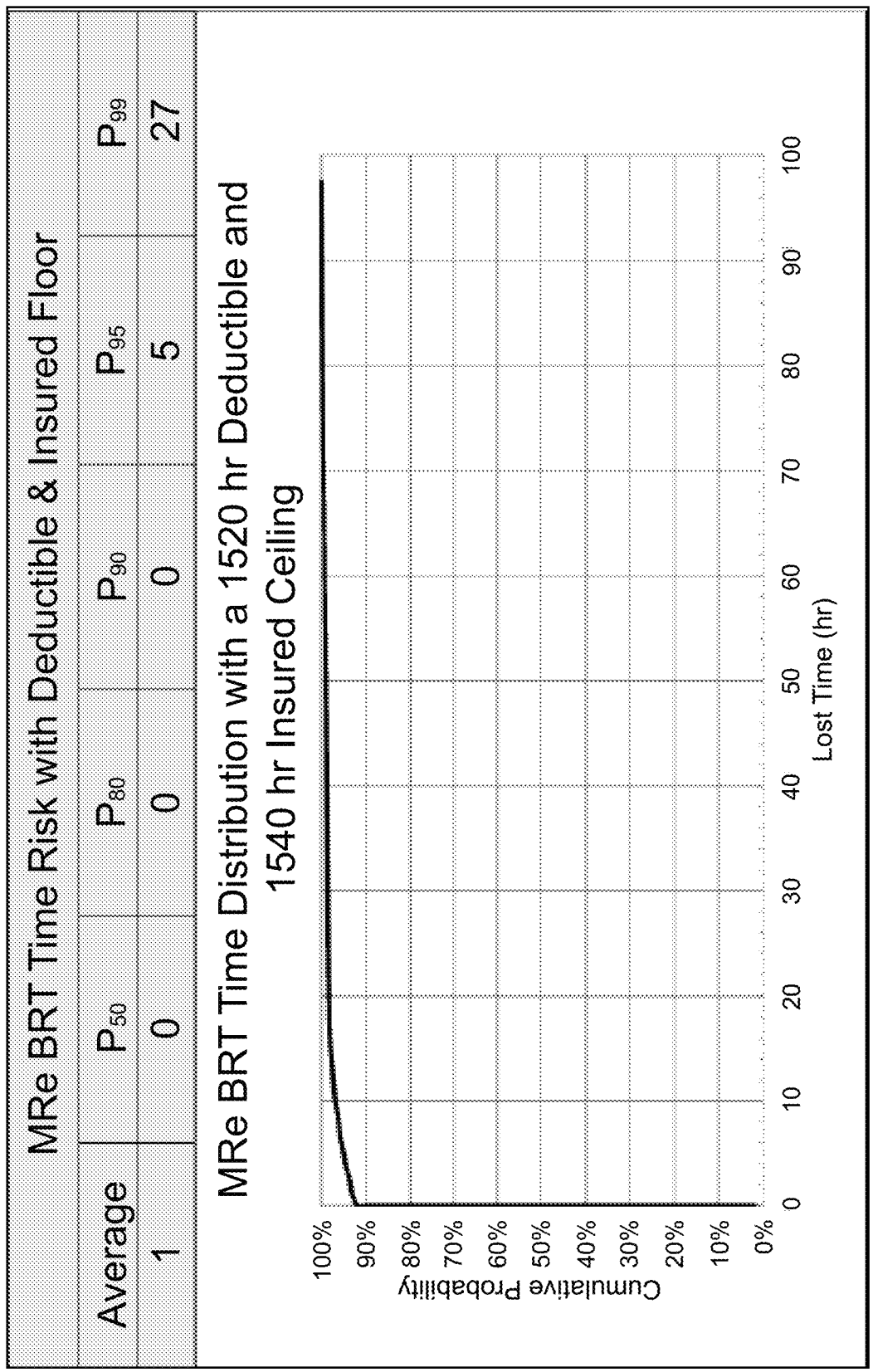
FIG. 10 illustrates an embodiment of when the well completion time risk greater than the time ceiling.

FIG. 10 illustrates when the well completion time risk is greater than the time ceiling. The last portion of the analysis displays the risk exposure transferred to an insurer in terms of insurance. The results show that there may be a low probability of occurrence associated with experiencing NPT results in excess of total BRT hours of about 1,540. However, the potential for relatively large NPT (and therefore relatively large BRT hours) results does exist. Mitigating these low frequency-high severity events may be the purpose of the insurance.

Programming and/or loading executable instructions onto memory 108 and processor 102 in order to transform the RTM processing system 100 into a particular machine or apparatus that utilizes the RTM is well known in the art. For example, the RTM processing system 100 may be implemented using macros within Microsoft Excel®. Implementing instructions, real-time monitoring, and other functions by loading executable software into a computer can be converted to a hardware implementation by well-known design rules. For example, decisions between implementing a concept in software versus hardware may depend on a number of design choices that include stability of the design and numbers of units to be produced and issues involved in translating from the software domain to the hardware domain. Often a design may be developed and tested in a software form and subsequently transformed, by well-known design rules, to an equivalent hardware implementation in an ASIC or application specific hardware that hardwires the instructions of the software. In the same manner as a machine controlled by a new ASIC is a particular machine or apparatus, likewise a computer that has been programmed and/or loaded with executable instructions may be viewed as a particular machine or apparatus.

At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations may be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). The use of the term "about" means ±±10% of the subsequent number, unless otherwise stated.

Use of the term "optionally" with respect to any element of a claim means that the element is required, or alternatively, the element is not required, both alternatives being within the scope of the claim. Use of broader terms such as comprises, includes, and having may be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present disclosure.

While several embodiments have been provided in the present disclosure, it may be understood that the disclosed embodiments might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

In addition, the various embodiments described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and may be made without departing from the spirit and scope disclosed herein.

What is claimed is:

1. An apparatus comprising:
an input interface;
a user interface;
a non-productive time (NPT) event frequency database;
a non-transitory memory;
a processor coupled to the non-transitory memory and configured to obtain and execute computer executable instructions stored on the non-transitory memory so as to cause the apparatus to perform at least the following:
receive drilling data for a drilling operation that corresponds to a plurality of planned runs of drilling equipment for the drilling operation;
determine a current NPT performance value for the drilling run based on the drilling data;
apply at least one category criteria to the drilling data to map the drilling data to at least one planned run category;
wherein the at least one category criteria comprises a plurality of predetermined category definitions to drilling data values;
determine one or more statistical simulations for the drilling operation to estimate a future NPT performance value associated with the drilling operation based on:
the current NPT performance value and the drilling data;
generate an NPT risk value based at least in part on the drilling data value;
wherein the NPT risk value maps NPT event severity as a function of NPT event frequency;
generate a planned drilling run iso-risk contour associated with the NPT risk value based at least in part on at the current NPT performance value and an estimated future NPT performance value;
determine an NPT risk modifier value based at least in part on the planned drilling run iso-risk contour;
determine a below rotary table (BRT) hours value for the drilling operation based on the current NPT performance value, the estimated future NPT value and the NPT modifier value;
generate a transfer model for the drilling run based on result data of one or more statistical simulations that estimate at least one actual downtime value associated with the plurality of planned runs based at least in part on the drilling data for the drilling operation;
determine a total non-productive time risk data for the plurality of planned runs based on the result data of the one or more statistical simulations and the transfer model;
wherein the total non-productive time risk data comprises at least one NPT probability distribution value;
predict a future non-productive time performance based on a score predicted by the transfer model;
generate a completion distribution associated with time to complete a well based at least in part on the total non-productive time risk data, the estimated future NPT performance value, and the current NPT performance data; and
generate and store a completion distribution record comprising a minimum level of performance, based at least in part on the well completion time distribution and the transfer model;
update the completion distribution record based on an analysis of the minimum level of performance associated with the completion distribution and the transfer model;
update the user interface with the completion distribution record to allow for a manipulation of at least one tool associated with the performance of the plurality of planned runs based on the minimum level of performance, the current NPT performance value, and the transfer model,
wherein the manipulation of the at least one tool associated with the performance of the plurality of planned runs comprises a real-time adjustment of the at least one tool at a predetermined period of time; and
output, via the user interface, a graphic display of a result of the manipulation of the at least one tool as a modification to the drilling data,
wherein a result of the manipulation may comprise a halt to a planned run.

2. The apparatus of claim 1, wherein the at least one statistical method for the operation is based on a number of Monte Carlo trials received as an input parameter via the input interface.

3. The apparatus of claim 1, wherein the future NPT performance value is based on a non-productive time event frequency parameter and a non-productive time severity parameter associated with the one or more planned runs.

4. The apparatus of claim 3, wherein the non-productive time event frequency parameter is a function of a bottom hole assembly configuration parameter.

5. The apparatus of claim 3, wherein the non-productive time severity is a function of a hole size parameter, a depth parameter, a drilled length parameter, and a maximum dog leg parameter associated with the drilling run.

6. The apparatus of claim 3, wherein the non-productive time severity for the drilling operation is multiplied by a binary frequency function to compute a non-productive time distribution in the one or more statistical simulations for the drilling operation.

7. The apparatus of claim 1, wherein the generated transfer model comprises a location modifier factor to account for a specific country or field.

8. The apparatus of claim 1, wherein the at least one drilling data variable generated transfer model comprises land and offshore non-productive time.

9. A system, comprising:
a memory configured to store computer code; and
a processor configured to execute the computer code stored in the memory that causes the processor to:
receive drilling data for a drilling operation that corresponds to a plurality of planned runs of drilling equipment for the drilling operation;
determine a current NPT performance value for the drilling run based on the drilling data;
apply at least one category criteria to the planned drilling data to map the planned drilling data to at least one planned run category;
wherein the at least one category criteria comprises a plurality of predetermined category definitions to drilling data values;
determine one or more statistical simulations for the at least one planned run to estimate a future NPT performance value associated with the at least one planned drilling run based on:
the current NPT performance value and the planned drilling data;
generate an NPT risk value based at least in part on the at least one drilling data value for the at least one drilling data variable;
wherein the NPT risk value maps NPT event severity as a function of NPT event frequency;
generate a planned drilling run iso-risk contour associated with the NPT risk value based at least in part on at the current NPT performance value and an estimated future NPT performance value;
determine an NPT risk modifier value based at least in part on the planned drilling run iso-risk contour;
determine a below rotary table (BRT) hours value for the at least one planned drilling run based on the current NPT performance value, the estimated future NPT value and the NPT modifier value;
generate a transfer model for the drilling run based on result data of the one or more statistical simulations-to-estimate at least one actual downtime value associated with the drilling data-for-the drilling run—that corresponds to the plurality of planned runs;
determine a total non-productive time risk data for the plurality of planned runs based on the result data of the one or more statistical simulations and the transfer model;
wherein the total not-productive time risk data comprises at least one NPT probability distribution value;
predict a future non-productive time performance based on a score predicted by the transfer model;
generate a completion distribution associate with time to complete a well based at least in part on the total non-productive time risk data, the estimated future NPT performance value, and the current NPT performance data; and
generate and store a completion distribution record comprising a minimum level of performance, based at least in part on the completion distribution and the transfer model;
update the completion distribution record based on an analysis of the minimum level of performance associated with the completion distribution and the transfer model;
update the user interface to allow for a manipulation of at least one tool associated with the performance of the plurality of planned runs based on the minimum level of performance, the current NPT performance value, and the transfer model,
wherein the manipulation of the at least one tool associated with the performance of the plurality of planned runs comprises a real-time adjustment of the at least one tool at a predetermined period of time; and
output, via the user interface, a graphic display of a result of the manipulation of the at least one tool as a modification to the drilling data,
wherein a result of the manipulation may comprise a halt to a planned run.

10. The system according to claim 9, wherein the at least one Monte Carlo trial is received as an input parameter via the input interface.

11. The system according to claim 9, wherein the future NPT performance value is based on a non-productive time event frequency parameter and a non-productive time severity parameter associated with the one or more planned runs.

12. The system according to claim 11, wherein the non-productive time event frequency parameter is a function of a bottom hole assembly configuration parameter.

13. The system according to claim 11, wherein the non-productive time severity is a function of a hole size parameter, a depth parameter, a drilled length parameter, and a maximum dog leg parameter associated with the drilling run.

14. The system according to claim 11, wherein the non-productive time severity for the drilling run is multiplied by a binary frequency function to compute a non-productive time distribution in the one or more statistical simulations for the drilling run.

15. The system according to claim 9, wherein the generated transfer model comprises a location modifier factor to account for a specific country or field.

16. The system according to claim 9, wherein the generated transfer model comprises land and offshore non-productive time.

17. A computer-implemented method comprising:
obtaining drilling data for a drilling run of drilling equipment for a well drilling operation;

determining a current non-productive time (NPT) performance for the drilling run based on the drilling data;

obtaining planned drilling data for at least one planned run following the drilling run;
  wherein the planned drilling data comprises at least one of:
    at least one hole size,
    at least one maximum depth, or
    at least one drilled length;

applying at least one category criteria to the planned drilling data to map the planned drilling data to at least one planned run category;
  wherein the at least one category criteria comprises a plurality of predetermined category definitions to drilling data values;

performing one or more statistical simulations for the at least one planned run to estimate future NPT associated with the at least one planned drilling run based on:
  at least one Monte Carlo trial using the at least one particular NPT distribution, and
  the planned drilling data;

accessing at least one external database comprising a plurality of operation reports associated with a plurality of drilling operations;

extracting from the plurality of operation reports at least one drilling data value for at least one drilling data variable;

generating an NPT risk value based at least in part on the at least one drilling data value for the at least one drilling data variable;
  wherein the NPT risk value maps NPT event severity as a function of NPT event frequency;

generating a planned drilling run iso-risk contour on the NPT risk value based at least in part on at least one planned drilling data value for the at least one drilling data variable for the at least one planned drilling run;

determining an NPT modifier value based at least in part on the planned drilling run iso-risk contour;

determining a below rotary table (BRT) hours value for the at least one planned drilling run based on the current non-productive time performance, the future NPT and the NPT modifier value;

generating a completion distribution associated with a time to complete a well based at least in part on the BRT hours value and the current NPT performance; and generate and store a completion distribution record comprising a minimum level of performance, based at least in part on the completion distribution;

updating the completion distribution record based on an analysis of the minimum level of performance associated with the completion distribution and the transfer model;

updating a user interface to allow for a manipulation of at least one tool associated with the performance of the plurality of planned runs based on the minimum level of performance, the current NPT performance value, and the transfer model,
  wherein the manipulation of the at least one tool associated with the performance of the plurality of planned runs comprises a real-time adjustment of the at least one tool at a predetermined period of time; and outputting, via the user interface, a graphic display of a result of the manipulation of the at least one tool as a modification to the drilling data,
  wherein a result of the manipulation may comprise a halt to a planned run.

18. The method of claim 17, wherein the future NPT is based on a non-productive time event frequency parameter and a non-productive time severity parameter associated with the one or more planned runs.

19. The method of claim 18, wherein the non-productive time event frequency parameter is a function of a bottom hole assembly configuration parameter.

20. The method of claim 18, wherein the non-productive time severity is a function of a hole size parameter, a depth parameter, a drilled length parameter, and a maximum dog leg parameter associated with the drilling run.

* * * * *